United States Patent [19]
Bornzin

[11] Patent Number: 5,766,229
[45] Date of Patent: Jun. 16, 1998

[54] CAPTURE VERIFICATION METHOD AND APPARATUS FOR IMPLANTABLE PACEMAKER UTILIZING HEART RHYTHM STABILITY MEASUREMENTS TO MINIMIZE THE LIKELIHOOD OF FUSION

[75] Inventor: Gene A. Bornzin, Simi Valley, Calif.

[73] Assignee: Pacesetter, Inc., Sylmar, Calif.

[21] Appl. No.: 837,144

[22] Filed: Apr. 14, 1997

Related U.S. Application Data

[60] Provisional application No. 60/015,973 Apr. 15, 1996.
[51] Int. Cl.$^6$ .................................................. A61N 1/362
[52] U.S. Cl. .................................................. 607/28; 607/16
[58] Field of Search .................................. 607/28, 16, 27

[56] References Cited

U.S. PATENT DOCUMENTS

| | | |
|---|---|---|
| 3,949,758 | 4/1976 | Jirak ............................................ 607/28 |
| 4,686,988 | 8/1987 | Sholder . |
| 4,712,555 | 12/1987 | Thornander et al. . |
| 4,788,980 | 12/1988 | Mann et al. . |
| 4,809,697 | 3/1989 | Causey et al. . |
| 4,815,469 | 3/1989 | Cohen et al. . |
| 4,817,605 | 4/1989 | Sholder . |
| 4,847,617 | 7/1989 | Silvian . |
| 4,878,497 | 11/1989 | Callaghan et al. ........................ 607/28 |
| 4,940,052 | 7/1990 | Mann et al. . |
| 4,944,298 | 7/1990 | Sholder . |
| 4,955,376 | 9/1990 | Callaghan et al. ........................ 607/28 |
| 4,969,462 | 11/1990 | Callaghan et al. ........................ 607/28 |
| 4,969,467 | 11/1990 | Callaghan et al. ........................ 607/28 |
| 5,417,718 | 5/1995 | Kleks et al. ............................... 607/28 |

*Primary Examiner*—William E. Kamm
*Assistant Examiner*—Kennedy J. Schaetzle

[57] ABSTRACT

An implantable pacemaker effectuates a capture verification method that minimizes the expenditure of battery current. A capture verification test is performed only occasionally, on a sampled basis, following delivery of a stimulation pulse. If capture is not verified, a loss of capture response mode is invoked that searches for an appropriate capture threshold, and when found, sets the stimulation energy at a level that is a prescribed safety factor above the capture threshold. All testing for capture is performed only after the heart rhythm has been measured, a short test pacing interval is selected that will be likely to overdrive the native rhythm, and the test pacing pulse delivered is delivered at the shortened interval so that the likelihood of fusion will be minimal.

21 Claims, 8 Drawing Sheets

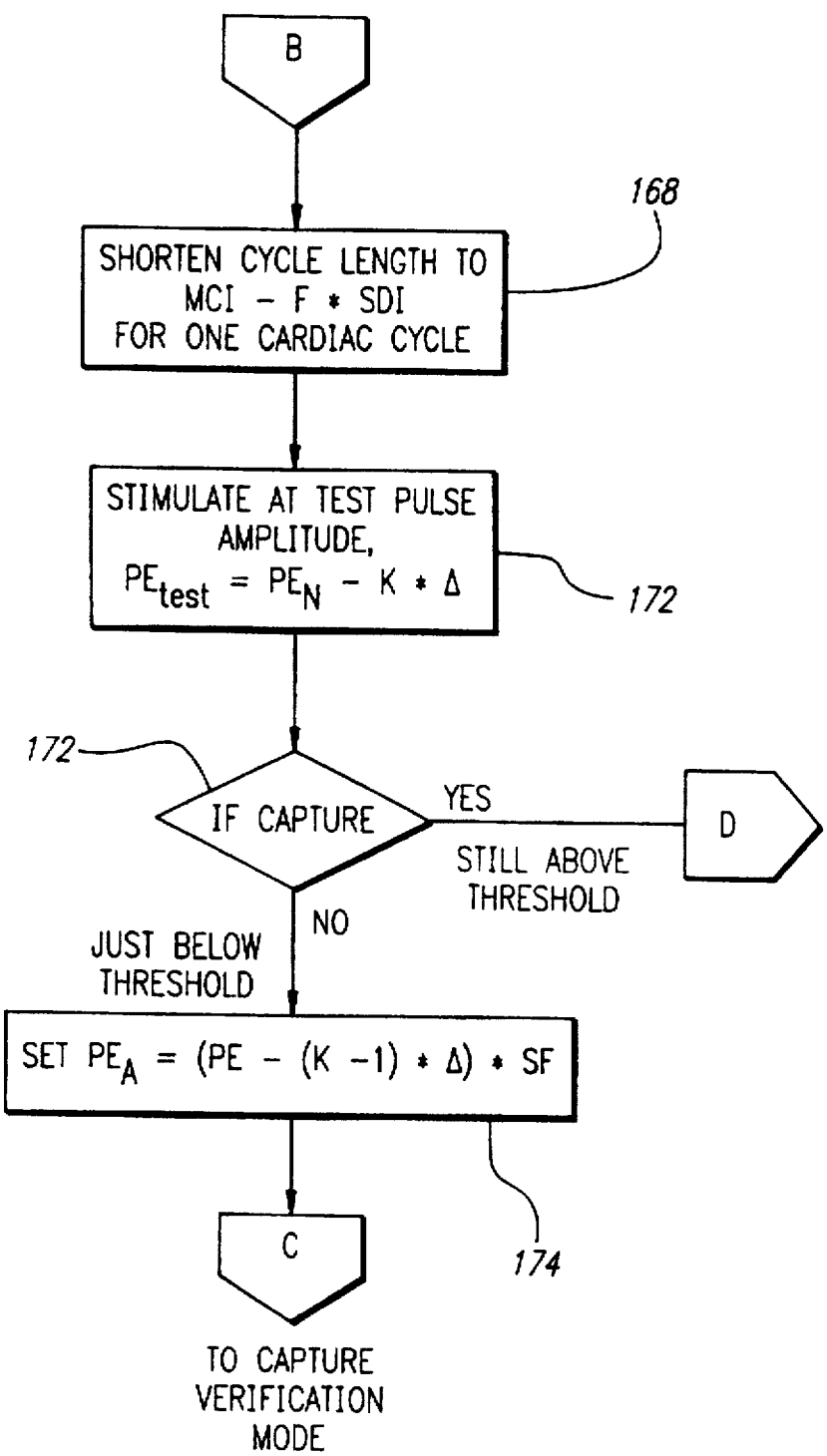

CAPTURE VERIFICATION METHOD AND APPARATUS FOR IMPLANTABLE PACEMAKER UTILIZING HEART RHYTHM STABILITY MEASUREMENTS TO MINIMIZE THE LIKELIHOOD OF FUSION

This application claims the benefit of Provisional Application No. 60/015,973, filed Apr. 15, 1996.

FIELD OF THE INVENTION

The present invention relates to implantable medical devices and methods, and more particularly to method of verifying capture without oversampling and with reduced likelihood of fusion interference.

BACKGROUND OF THE INVENTION

Implantable pacemakers generate electrical stimulation pulses and deliver such stimulation pulses to atrial and/or ventricular muscle tissue of a patient's heart at a prescribed rate and/or rhythm when, through disease or other causes, the heart is not able to maintain the prescribed heart rate or rhythm on its own. When the delivered electrical stimuli are of sufficient energy, they cause the cardiac muscle tissue to depolarize, and therefore contract, thereby forcing the heart rate or rhythm to track the delivery of the electrical stimuli. When the delivered electrical stimuli are of insufficient energy, depolarization does not occur, and the heart rate or rhythm is not controlled by the pacemaker. Hence, for the pacemaker to perform its intended function, it is critically important that the delivered electrical stimuli be of sufficient energy to depolarize the cardiac tissue, a condition known as "capture".

The energy of the electrical stimuli generated by an implanted pacemaker is derived from the energy stored in the pacemaker's battery. The pacemaker's battery has a limited amount of energy stored therein, and the generation of electrical stimuli represents by far the greatest drain of such energy. In order to preserve this limited energy and prolong the life of the battery, it is known in the art to adjust the energy of the delivered electrical stimuli so that it is just sufficient to cause capture, with an appropriate safety margin. See, e.g., U.S. Pat. Nos. 3,949,758 and 4,686,988. The amount of energy needed to effectuate capture is known as the capture "threshold", and electrical stimuli of energy less than the capture threshold do not bring about capture, while electrical stimuli of energy greater than the capture threshold do bring about capture. By adjusting the energy of the electrical stimuli so that it is always greater than the capture threshold, but not too much greater, the limited energy of the pacemaker battery may thus be preserved. The battery energy is preserved because: (1) electrical stimuli of insufficient energy to cause capture (electrical stimuli below threshold), which stimuli represent wasted energy, are rarely generated; and (2) electrical stimuli of excessive energy (energy much greater than the capture threshold), which excess energy not only represents wasted energy, but also energy that may disadvantageously cause pectoral stimulation and/or sensation, are also rarely generated.

In general, the teaching of the prior art on capture verification has regarded capture verification as a process that must be carried out continually. The prior art teaches that capture must be verified with each and every stimulus so that a servomechanism within the pacemaker can provide a backup pulse in the event that a first pulse fails to provide capture, and/or so that the energy of the next stimulation pulse can be adjusted upward. See, e.g., U.S. Pat. Nos. 4,969,467; 4,969,462; and 4,955,376. A capture verification process that is vigilant at all times to automatically maintain capture in this manner may be referred to as an "autocapture" process.

Unfortunately, capture verification is not a simple, failsafe, process. Not only must a significant amount of processing time, and corresponding battery current, be expended in order to complete a capture verification procedure, but many events can occur that can confound the autocapture process. One such event, for example, is fusion. A fusion depolarization is triggered in part by a spontaneous depolarization and in part by a pacing stimulus. Unfortunately, when fusion occurs, the evoked potential (the electrical signal manifest upon the occurrence of depolarization, e.g., usually a P-wave or an R-wave) may be diminished in size or completely absent. Hence, a fusion beat may easily be misclassified by the autocapture circuits as a loss of capture.

In order to prevent misclassifying a fusion beat as a loss of capture, it is possible to shorten the next pacing cycle or cycles, and then recheck to see if the next pacing stimulus results in a loss of capture. The rational for this approach is that if the pacing cycle length is shortened, then the likelihood of another fusion becomes small. Other teachings for preventing the misclassifying of a fusion beat include providing a backup stimulation pulse immediately following an apparent loss of capture and checking for an evoked potential. An evoked potential following a backup pulse implies the "loss of capture event" was real; while no evoked potential following the backup pulse implies the "loss of capture event" was a fusion. See, e.g., U.S. Pat. Nos. 4,969,647; 4,969,462; 4,878,497; and 4,955,376. Disadvantageously, providing a backup stimulation pulse in this manner not only represents the expenditure of additional energy, thereby further shortening the battery's life, but may also cause pectoral stimulation or cause other undesirable effects for the patient, including increasing the likelihood of fusion.

An important part of capture verification is the determination that an evoked potential has occurred. (Note, an "evoked potential" is the depolarization signal that immediately follows a pacing stimulus when the pacing stimulus is of sufficient energy to bring about "capture". The evoked potential may be thought of as a paced P-wave or paced R-wave. It should also be noted that a paced P-wave or paced R-wave, when viewed on an electrogram or electrocardiogram, does not usually have the same appearance as an intrinsic or spontaneous atrial depolarization or ventricular depolarization, i.e., a paced R-wave or paced P-wave does not appear the same as an intrinsic or natural P-wave or R-wave.) The prior art teaches that evoked potential sensing is best performed in a ring-to-case (R—C) electrode configuration, rather than in the tip-to-ring (T-R) or tip-to-case (T—C) electrode configuration, which T-R and T-C configurations are more commonly used for pacemaker sensing and pacing. See, e.g., U.S. Pat. Nos. 4,686,988 and 4,817,605, incorporated herein by reference. Hence, in the prior art, it is common to switch the electrode configurations back and forth every beat between the normal preprogrammed sensing configuration, T-R, to the evoked potential configuration, R-C. Disadvantageously, such frequent electrode configuration switching leads to periods of "inhibition sensing blindness" (or forced system refractory periods) due to the fact that switching cycles usually must take place over clock cycle multiples of several msec., e.g., 6.25 msec, and further due to the relatively long settling time of the sense amplifiers (which settling time may itself be up to 80 msec long).

In view of the above, it is evident that what is needed is a capture verification method that minimizes the expenditure of battery current, reduces or eliminates frequent switching of electrode sensing configurations, and that reduces the risk of fusion interference and/or other undesirable side effects.

SUMMARY OF THE INVENTION

The present invention addresses the above and other needs by providing an implantable pacemaker wherein a capture verification test is performed only occasionally, on a sampled basis, following delivery of a stimulation pulse. If capture is not verified, a loss of capture response mode is invoked that searches for the capture threshold. When found, the stimulation energy of the pacemaker is set at a level that is a prescribed safety factor above the capture threshold.

All testing for capture in accordance with the present invention is performed only when a sustained heart rate has been maintained for some period of time, and by then stimulating with a reduced cycle length having an interval much shorter than the sustained rate interval. Such testing, because it is performed on a not-too-frequent basis, i.e., a sampled basis, advantageously limits the time and power needed by the electronic circuitry (typically a microprocessor) to perform the test, thereby conserving power and freeing up the circuitry for other processes, and further significantly reduces the likelihood of fusion.

Thus, in accordance with one aspect of the invention, the expenditure of battery current in the pacemaker is minimized because capture is verified only occasionally, not every cycle as is commonly done in the prior art. Further, the expenditure of battery current is minimized by not generating any stimulation pulses, nor performing any capture threshold tests, unless the heart rhythm has stabilized, thereby avoiding potentially meaningless testing and ineffective stimulation.

A further aspect of the invention provides for capture verification without frequent switching of the electrode sensing configuration, and thus without promoting a system that is deliberately made refractory with every beat, and therefore without creating frequent sensing "blind spots", as is common in the prior art.

Another aspect of the invention reduces the likelihood of fusion interfering with the capture verification process. This is because capture is verified only occasionally, not every cycle, and only after certain stability criteria have been met.

It is thus seen that the present invention addresses the capture verification problem using a different premise than that used in the prior art, namely, capture does not need to be verified every time the heart is stimulated, but merely needs to be verified very few minutes while maintaining a small but adequate safety margin. Hence, the present invention recognizes that the prior art approach of verifying capture every beat is much like "oversampling a function", which oversampling introduces numerous inefficiencies and other problems.

The invention may thus be characterized as a capture verification method that includes: (a) monitoring a heart rate of a patient to ascertain if the heart rate is within a prescribed tolerance of a base rate, where the base rate corresponds to a base cardiac cycle length; (b) providing an electrical stimulus to the heart at a shortened pacing cycle length only when the monitoring of step (a) indicates that the heart rate is stable, i.e., only when the heart rate has remained within a prescribed tolerance of the base rate for a specified number of cardiac cycles; and (c) sensing whether an evoked potential occurs following the electrical stimulus provided in step (b), and if so, verifying that capture has occurred.

It is therefore a feature of the present invention to provide a method for verifying, without oversampling, and therefore without needless switching to capture verification and threshold searching modes, that an implantable pacemaker achieves capture with the stimulation pulses that it generates.

The invention may also be characterized as an implantable pacemaker that includes circuitry for automatically carrying out the above method.

It is thus a feature of the invention to provide a method, automatically invoked by an implantable pacemaker whenever loss of capture is detected, that searches for an appropriate capture threshold, and that when found, sets the stimulation energy of the pacemaker at a level that is an adequate safety factor above the capture threshold.

It is still a further feature of the invention to provide an implantable pacemaker wherein capture verification tests are performed by the pacemaker only on a sampled basis, and only when certain stability criteria have been maintained relative to the cardiac rhythm, thereby minimizing the likelihood of fusion interfering with the capture verification process.

It is yet another feature of the invention to provide such an implantable pacemaker wherein capture verification tests are followed, when needed, with capture threshold tests that accurately determine the capture threshold and set the stimulation pulse energy to a new value above the capture threshold.

BRIEF DESCRIPTION OF THE DRAWINGS

The above and other aspects, features and advantages of the present invention will be more apparent from the following more particular description thereof, presented in conjunction with the following drawings wherein:

FIGS. 7–9 describe the various details of the method blocks shown in FIG. 6.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention is directed primarily to a method of verifying capture on a sampled basis, and (when capture is not verified) of measuring the capture threshold, and resetting the stimulation energy to a value that is equal to the capture threshold plus a safety margin. Such methods are best implemented by the circuitry within an implantable pacemaker. Hence, before describing the methods that comprise the present invention, it will first be helpful to briefly describe the circuitry that is included within an implantable pacemaker that is used to carry out such methods.

Thus, reference will first be made to FIG. 1, where a functional block diagram of a dual-chamber pacemaker 10 is illustrated. Such functional diagram is used to initially teach the primary functions carried out by a dual chamber pacemaker. Various embodiments of the actual components used within the pacemaker 10 to carry out the pacemaker functions will then be described in conjunction with FIGS. 2–4. The capture verification method, and capture threshold measuring method invoked when capture is not verified, will then be described in connection with the flowcharts of FIGS. 5 and 6.

It should also be noted that the pacemaker circuits that are described below in FIGS. 1–4 are for a dual-chamber pacemaker, i.e., a pacemaker that is capable of sensing and/or pacing within two channels, with each channel being coupled to either the atrium or the ventricle of the heart. It should be understood, however, that the present invention is not limited to use with a dual-chamber pacemaker. Rather, the invention may be implemented using either a dual-chamber or a single-chamber pacemaker. A single-chamber pacemaker is, as its name implies, a pacemaker that senses and/or paces in only one chamber of the heart. As such, the circuitry of a single-chamber pacemaker is the same as a portion of the circuitry of a dual-chamber pacemaker. That is, the single-chamber pacemaker includes circuitry for one channel (atrial or ventricular) whereas the dual-chamber pacemaker includes circuitry for two channels (atrial and ventricular).

Figure 1:
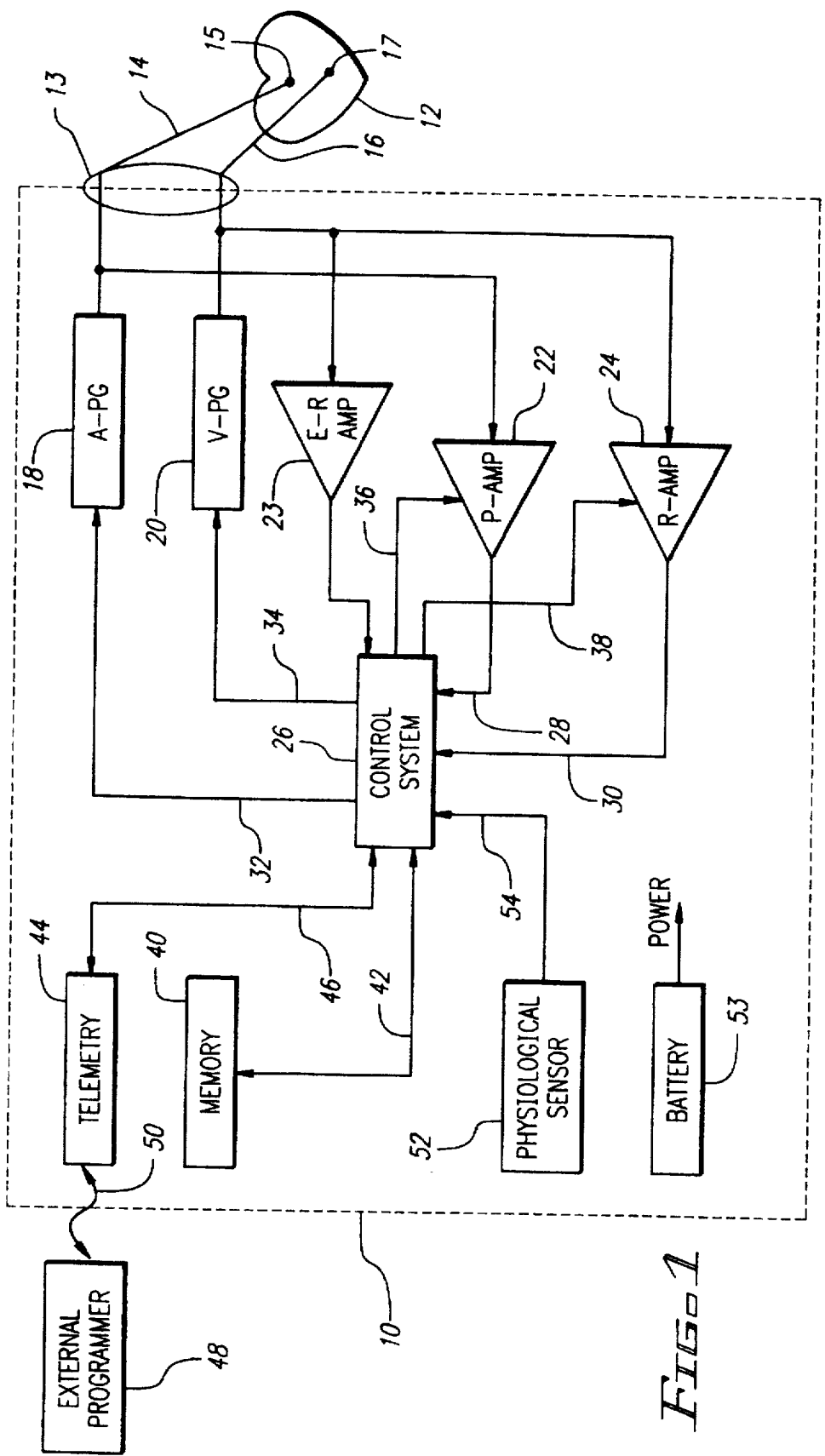
FIG. 1 is a functional block diagram of an implantable dual-chamber pacemaker.

Referring then to FIG. 1, a functional block diagram of a dual-chamber pacemaker 10 is shown as being coupled to a heart 12 by way of leads 14 and 16. (Note, in subsequent figures, e.g., FIG. 2, the leads 14 and 16 are referred to as the lead system 19.) The lead 14 has an electrode 15 that is in contact with one of the atria of the heart, and the lead 16 has an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

An evoked-response (E-R) amplifier 23 is also shown as being coupled to the ventricular electrode 17 by way of the lead 16. The E-R amplifier 23 is configured to sense the evoked response (paced V-pulse) immediately following a ventricular stimulus ("V-pulse"). While the E-R amplifier is shown as being coupled to the ventricular electrode 16, it should be understood that the E-R amplifier 23, or an additional E-R amplifier, could be coupled to the atrial electrode 15, in order to sense the evoked response (paced A-pulse) immediately following an atrial stimulus ("A-pulse"). The use of an E-R amplifier 23 is described more fully in U.S. Pat. Nos. 4,686,988 or 4,817,605, previously incorporated herein by reference. It should also be noted that the use of the E-R amplifier 23 is not mandatory, as the evoked response may also be sensed through the normal sensing amplifiers for the respective channels, i.e., the P-AMP 22 or the R-AMP 24.

Sensing and pacing occur in conventional manner, using a unipolar, bipolar, or ring-to-case electrode configuration. That is, for either sensing or pacing to take place, there must be a reference electrode (not shown in FIG. 1) to provide an electrical return path for the signal that is being sensed, or for the stimulus that is being delivered. In unipolar sensing/pacing, such reference electrode is provided as part of the case of the pacemaker 10, with the electrical signal being sensed or applied between a tip (T) electrode of the lead and the case (C) of the pacemaker (with an electrical return path thus being provided through the conductive body fluids between the heart and the case). Unipolar pacing may thus be referred to as a T-C (tip-to-case) electrode configuration. In bipolar pacing, a ring (R) electrode is provided as part of the respective lead a short distance (1–2 cm) from the tip electrode at the end of the lead. Pacing and sensing thus occurs between the tip (T) electrode and the ring (R) electrode, or in a T-R configuration. Evoked potentials are generally best sensed using a ring-to-case (R-C) electrode configuration. The electrode configuration of a given pacemaker may be fixed, or programmable.

Controlling the dual-chamber pacer 10 is a control circuit or control system 26. The control system 26 receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control circuit or system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. A stimulation pulse generated by the A-PG 18 is referred to as the "A-pulse," and the stimulation pulse generated by the V-PG 20 is referred to as the "V-pulse." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large A-pulse or V-pulse, respectively, that is present at the input terminals of such amplifiers during this time. Such blanking action also helps prevent residual electrical signals present in the muscle tissue as a result of the pacer stimulation from being interpreted as P-waves or R-waves. (In contrast, when an evoked potential is sensed, particularly when sensed when using an R-C electrode configuration, the blanking signals are either not used to blank the E-R amp, or are made much shorter than normal so as to allow an evoked response to be sensed.)

Still referring to FIG. 1, the pacemaker 10 also includes a memory circuit 40 that is coupled to the control system 26 over a suitable data/address bus 42. The memory circuit 40 allows certain control parameters, used by the control system 26 in controlling the operation of the pacemaker, to be programmably stored and modified, as required, in order to customize the pacer's operation to suit the needs of a particular patient. Such data includes the amplitude of the A-pulse or V-pulse that is to be generated by the A-PG 18 or the V-PG 20, the sensing threshold of the P-AMP 22, R-AMP 24, or E-R AMP 23, the electrode configuration, and the basic timing intervals used during operation of the pacemaker, as is known in the art. Further, data sensed during the operation of the pacer may be stored in the memory 40 for later retrieval and analysis.

A telemetry circuit 44 is also provided within the pacemaker 10. This telemetry circuit 44 is connected to the control system 26 by way of a suitable command/data bus 46. The telemetry circuit 44 may be selectively coupled to an external programming device 48 by means of an appropriate communication link 50. The communication link 50 may be any suitable electromagnetic link, such as an RF (radio frequency) channel, inductive coupling, or the like. Advantageously, through the external programmer 48 and the communication link 50, desired commands may be sent to the control system 26, such as the initial amplitude of the A-pulse or V-pulse that is to be generated by the A-PG 18 or the V-PG 20. Advantageously, once the energy content (e.g., amplitude and/or pulse width) of the A-pulse and the V-pulse have been initially set or programmed, the present invention allows changes to be made thereto, as required, in order to measure the capture threshold and/or to set the pulse energy of future stimulation pulses to a value that is above the measured capture threshold by a prescribed safety margin. Also, through the communication link 50 and the programmer 48, data (either held within the control system 26, as in a data latch, or stored within the memory 40), may be remotely received from the pacer 10. In this manner, non-invasive communications may be established from time to time with the implanted pacer 10 from a remote, non-implanted location. There are many suitable telemetry circuits known in the art that may be used with the present invention for the telemetry circuit 44. See, e.g., U.S. Pat. No. 4,847,617, incorporated herein by reference.

The pacer 10 in FIG. 1 is referred to as a dual-chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the atrial channel. Similarly, those portions of the pacer 10 that interface with the ventricles, e.g., the lead 16, the R-wave sense amplifier 24, the E-R AMP 23, the V-pulse generator 20, and corresponding portions of the control system 26, are commonly referred to as the ventricular channel. Throughout the discussion that follows, reference may be made to "atrial channel activity" or "ventricular channel activity." Atrial channel activity comprises either the sensing of a P-wave by the sense amplifier 22, or the generating of an A-pulse by the A-pulse generator 18. Similarly, ventricular channel activity comprises the sensing of an R-wave by the sense amplifier 24 or the sensing of an evoked response by the E-R AMP 23, or the generation of a V-pulse by the V-pulse generator 20. Further, as indicated above, a dual-chamber pacemaker is described herein only for completeness. The invention may also be used with a single-chamber pacemaker, i.e., a pacer having only an atrial channel or a ventricular channel.

In some pacemakers that implement the present invention, the pacemaker 10 may further include one or more physiological sensors 52 that is/are connected to the control system 26 of the pacer over a suitable connection line 54. While the sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, mounted to the case of the pacemaker. Other types of sensors as are known in the art, such as sensors that sense the oxygen content of blood, respiration rate, pH of blood, body motion, mechanical events (e.g., contracting of cardiac tissue), blood pressure, and the like, may also be used in lieu of, or in addition to, an activity sensor. Further, it is noted that some sensing functions do not require a separate "sensor" but may be performed simply using the circuitry within the pacemaker, such as measuring time intervals between certain events, or measuring electrical lead impedance, and the like. The type of sensor, if any, used is not critical to the present invention. Any sensor, or combination of sensors, capable of sensing some physiological or other parameter relatable to the rate at which the heart should be beating, or to the current status or condition of the patient, may be used. A pacemaker that uses such sensors to adjust the pacing rate (escape interval) of the pacemaker in a manner that tracks the physiological needs of the patient is commonly referred to as a "rate-responsive" pacemaker.

Figure 2:
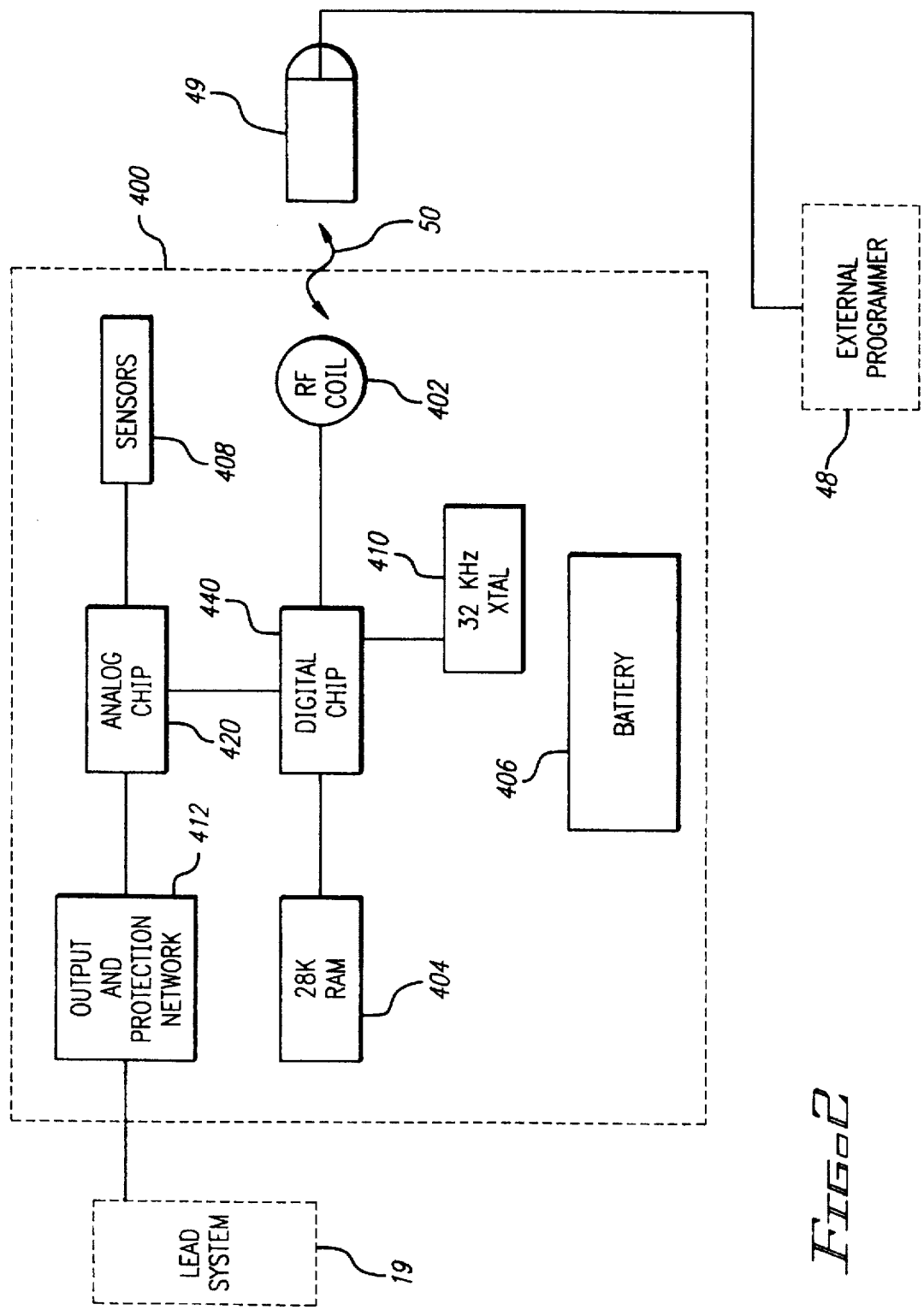
FIG. 2 is a block diagram of a pacing system that depicts the main hardware components of an implantable pacemaker.

In FIG. 2, there is shown a preferred configuration for a pacing system that may be used to implement the present invention. The system includes the external programmer 48, the implantable pacemaker 10, and the lead system 19. The lead system 19 includes conventional atrial and ventricular leads and electrodes, as described previously or as is known in the art. The lead system 19 may also include an oxygen sensor lead, which lead contains an LED-detector assembly used to measure the oxygen content of the blood. Such a lead is described, e.g., in U.S. Pat. No. 4,815,469, incorporated herein by reference.

The external programmer 48 includes a telemetry head 49 that is positioned proximate the implantable pacemaker 10 whenever the communication link 50 is to be established between the pacemaker 10 and the external programmer 48. The external programmer may be of conventional design, as described, e.g., in U.S. Pat. No. 4,809,697, incorporated herein by reference.

The components of the pacemaker 10 are housed within a suitable sealed case or housing 400 (which case or housing is represented in FIG. 2 by the dashed line 400). The case 400 is preferably a titanium metal case. The components within the case 400 include an RF coil 402, a memory chip 404, a battery 406, one or more sensors in a sensor circuit 408, a crystal 410, an output/protection network 412, an analog chip 420 and a digital chip 440.

The battery 406, which is by volume the largest component within the pacemaker 10, may be of conventional design, and is typically a lithium battery that provides operating power to all of the electronic circuits within the pacemaker. The RF coil 402 is used to establish the communication link 50 with the telemetry head 49. The crystal 410 is used in conjunction with a crystal oscillator circuit on the digital chip 440 (described below) to provide a stable clock frequency for the pacemaker circuits. In the preferred embodiment, the frequency of the crystal oscillator is 32 KHz, although any suitable frequency could be used. The sensor circuit 408 includes appropriate sensors used by the pacemaker as it carries out a rate-responsive pacing function, or as other needed parameters are measured. For example, in one embodiment, the sensor circuit 408 includes an accelerometer adapted to sense patient activity. Other sensors may also be used to, e.g., sense heart rhythm stability, such as a mechanical sensor (to sense physical contractions of the heart tissue), an impedance sensor (to sense changes in electrical impedance of the cardiac tissue and/or leads), a systolic pressure sensor (to sense blood pressure), and the like.

The memory chip 404 is a low-power static random access memory (RAM) chip wherein the operating parameters, e.g., control variables, of the pacemaker may be stored, and wherein sensed data may be stored, as required. The analog chip 420 and the digital chip 440 contain the main processing and control circuits of the pacemaker. These chips are advantageously designed to minimize the number of components needed external hereto for operation of the pacemaker. The analog chip 420 interfaces with the lead system 19 through the output and protection network 412, which network includes output capacitors, appropriate feed-through connectors to allow electrical connection through the hermetically sealed case, and the like, as are commonly used in implantable medical devices.

Figure 3:
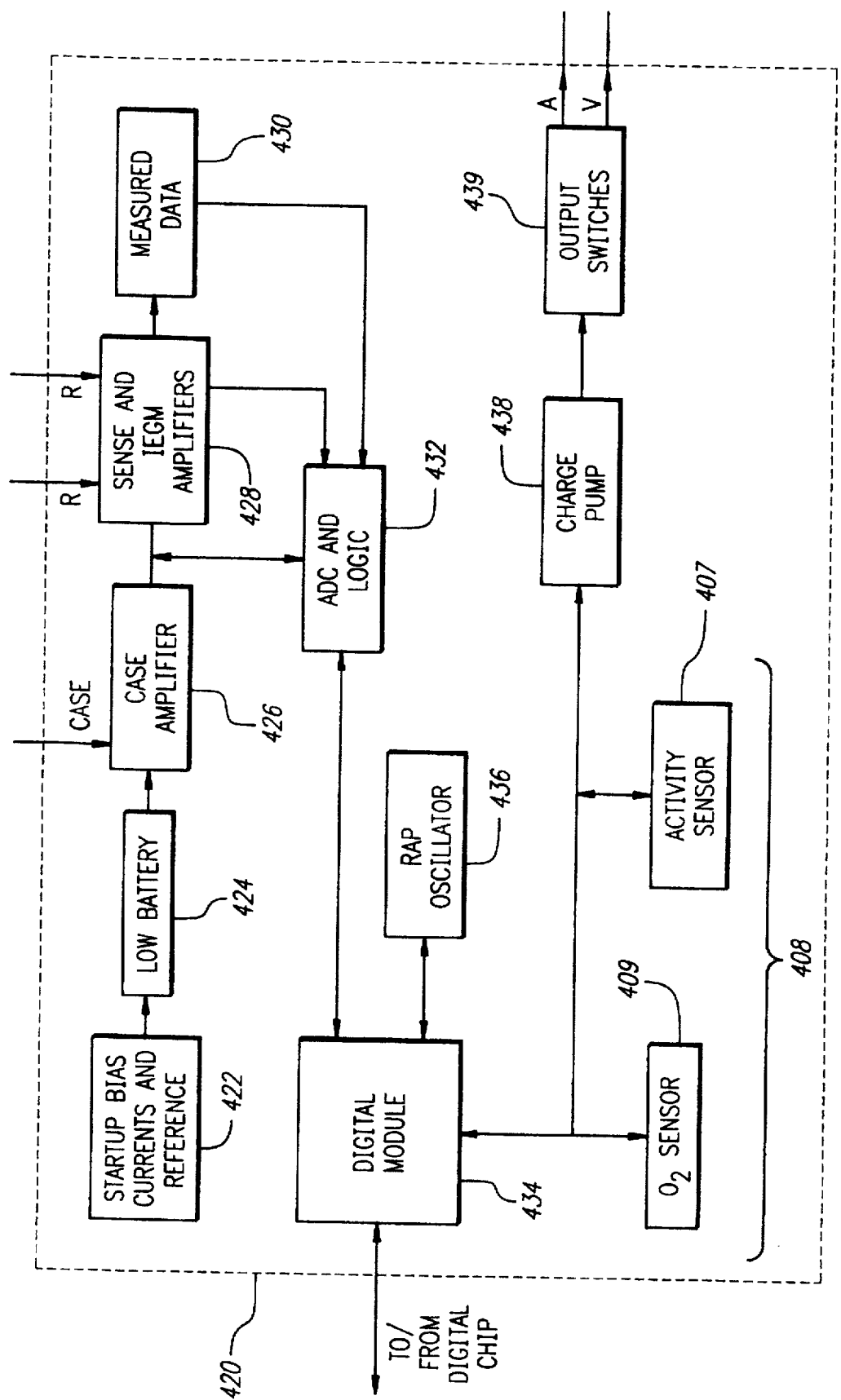
FIG. 3 is a block diagram of the analog chip portion of the pacemaker of FIG. 2.

In FIG. 3, a block diagram of the analog chip 420 is shown. The analog chip contains all the necessary subsystems and modules to interface to the lead system 19 and the digital chip 440. For example, a startup/bias-current/ reference module 422 contains the power-up signals used to initialize the pacer circuit when the battery is first applied. A low battery module 424 detects four voltage levels of the battery voltage for determining the battery status. A case amplifier 426 generates a CASE bias voltage that is used as a reference for the sense and IEGM (intracardiac electrogram) amplifier module 428. The module 428 includes the P-wave amplifier 22 and the R-wave amplifier 24, described above in FIG. 1. A measured data module 430 measures the battery voltage and current and other analog parameters of the pacing system. An ADC and Logic module 432 includes an analog-to-digital converter and timing logic that are used to convert the analog signals of the pacemaker in to 8-bit digital words. These digital words are then passed to a digital module 434, which module is used to generate all the basic timing and bus control functions as data is passed back and forth between the analog chip 420 and the digital chip 440.

Still referring to FIG. 3, it is seen that a Runaway Protection (RAP) circuit oscillator 436 is also coupled to the Digital Module 434. Such oscillator 436 provides an independent time base for limiting the highest pacing rate allowed by the pacemaker. Further coupled to the digital module 434 is the sensor network 408. The sensor network 408 includes appropriate sensors for sensing activity and other parameters. For example, an $O_2$ sensor circuit 409 may be used in conjunction with the oxygen sensor lead, when used, to measure blood oxygen of the patient. An activity sensor 408 may also be used to sense patient activity as measured, e.g., by an accelerometer. A charge pump circuit 438 generates the output voltages for the stimulation pulses that are delivered to the patient's heart. A network of output switches 439 connects the charge developed by the pump circuit 438 to the output leads at the appropriate time to form the appropriate stimulation pulses.

It is thus seen that the analog chip 420 contains the necessary circuitry to sense and detect atrial or ventricular events, digitize IEGM waveforms, measured data and other various analog signals, and provide such sensed and digitized signals to the digital module 434 for use by the digital chip 440. The charge pump circuit 438 acts as a voltage doubler/tripler for high output pulse capability. The output pulse width is controlled by the output switches 439. The combination of the amplitude and width of the stimulation pulse controls the stimulation energy. The condition of the battery is monitored, and independent Runaway Protection is provided.

Figure 4:
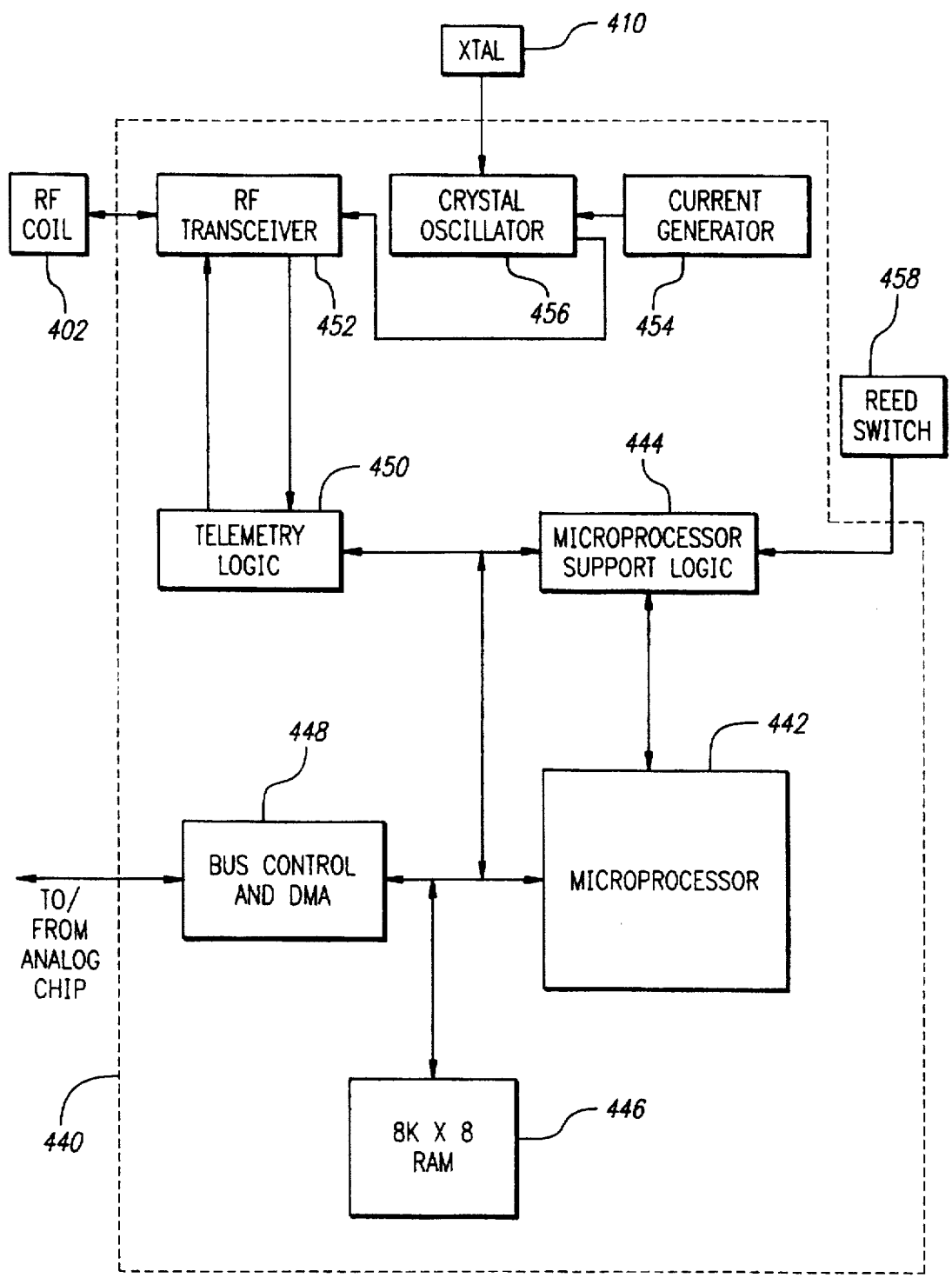
FIG. 4 is a block diagram of the digital chip portion of the pacemaker of FIG. 2, and illustrates the use of a microprocessor to control the operation of the pacemaker.

In FIG. 4, it is seen that the main control element of the pacemaker is a microprocessor 442, which microprocessor is included within the digital chip 440. The digital chip 440 contains all the necessary logic to interface the analog chip 420 with the internal microprocessor 442. The microprocessor 442 includes a basic CPU (central processing unit) and 8K of static RAM. In addition, an 8K by 8K RAM 446 is connected to the microprocessor 442 to store data and programs. Microprocessor support logic 444, also coupled to the microprocessor 442, includes interrupt logic, timer logic, noise/sensed event logic, and magnet status logic. A bus controller 448 is further included on the digital chip 440 to provide DMA timing and control of data transfer with the analog chip 420, including timing and control of the analog-to-digital converter 432 (FIG. 3) and telemetry data. Telemetry channel logic 450 contains clock logic, IEGM and marker logic, telemetry command protocol logic, telemetry interrupt logic, error checking logic and CPU reset logic. An RF transceiver 452, coupled to the RF coil 402, transmits and receives telemetry data from the external programmer 48 (see FIGS. 1 and 2 ) through the telemetry head 49 (see FIG. 2). A crystal oscillator circuit 456, in conjunction with the crystal 410 (external to the digital chip 440) provides the crystal time base of the pacemaker system. A current generator 454 provides the bias currents for the digital chip. A reed switch circuit 458 detects the presence of a magnetic field, which magnetic field is present whenever the telemetry head 49 is in place on the patient's skin above the location where the pacemaker is implanted.

The pacemaker circuitry described in connection with FIGS. 2–4 above provides the basic functions of the pacemaker described in connection with FIG. 1, plus other pacing/sensing functions as are known in the art. For purposes of the present invention, the pacemaker circuitry of FIGS. 2–4 sets the basic stimulation energy (pulse amplitude and width) of the A-pulse and/or V-pulse that is generated by the pacemaker. Further, such circuitry sets the timing of the pacing interval, including setting a PV interval (the time interval between an atrial event and a ventricular event), a VA interval (the time interval between a ventricular event and an atrial event), with the sum of the PV and VA intervals thus defining a pacing interval, or pacing cycle. The circuitry also provides for sensing or detecting natural ventricular events (R-waves) and/or natural atrial events (P-waves), as well as evoked responses (paced P-wave or paced R-wave) following delivery of an A-pulse and/or V-pulse. The circuitry further provides for measuring the time interval between sensed and/or paced events, e.g., a P-to-P interval, or a P-to-R interval, a V-to-P interval, a V-to-V interval, and the like.

In addition to the embodiment of the invention illustrated above in FIGS. 2–4, other embodiments of a control system 26 may be utilized. The embodiment described above in FIGS. 2–4 shows a control system and pacemaker configuration based on a microprocessor. Another representative microprocessor-based system is described, for example, in U.S. Pat. No. 4,940,052, entitled "Microprocessor Controlled Rate-Responsive Pacemaker Having Automatic Threshold Adjustment," incorporated herein by reference. Still other control systems may be based on a state machine wherein a set of state registers define the particular state of the pacer at any instant in time. As is known in the art, state machines may be realized using dedicated hardware logic circuits, or a suitable processor (programmed-controlled circuit) to simulate such dedicated hardware logic circuits. However implemented, the results are the same—the state of the pacer is defined at any instant of time by the pacemaker logic and sensed events which transpire or fail to transpire, such as the sensing of an R-wave, or the timing out of a timer. State machine operation, as is relates to control of a pacemaker, is described, for example, in U.S. Pat. Nos.

4,712,555 and 4,788,980, wherein the various timing intervals used within the pacemaker and their interrelationship are more thoroughly described; and U.S. Pat. No. 4,944,298, wherein an atrial-rate based programmable pacemaker is described, including a thorough description of the operation of the state logic used to control such a pacemaker. The '555, '980 and '298 patents are also incorporated herein by reference. (It should also be noted that, in a broad sense, a microprocessor is also a type of state machine, changing from one state to another as a function of a predefined operating program and the occurrence, or absence, or various sensed events.)

The details of the control system 26, whether based on a microprocessor, state machine, or other type of control devices, or simulated control devices, are not critical to an understanding or implementation of the present invention, and hence are not presented herein.

Such details may be found in the referenced applications and patents, if desired. All that is needed for purposes of the present invention is that the control system of the pacemaker, in conjunction with other pacemaker circuitry, be capable of: (1) setting the stimulation energy of the A-pulse and/or V-pulse by adjusting the amplitude and/or pulse width thereof; (2) sensing R-waves and/or P-waves, including an evoked response (e.g., a paced R-wave); (3) measuring and/or setting the time interval between specified sensed and/or paced events; and (4) monitoring whatever other sensors are employed to determine the stability of the cardiac rhythm.

Given a pacemaker constructed as described above in connection with FIGS. 1–4, or an equivalent pacemaker, the present invention relates generally to a method of verifying, on a sampled basis, that capture occurs in response to a delivered A-pulse or V-pulse; and for further measuring the capture threshold in the event that capture does not occur, and for thereafter setting the stimulation energy to a new value that exceeds the measured capture threshold by a prescribed safety margin. An overview of such a method is shown in the flowchart of FIG. 5.

Figure 5:
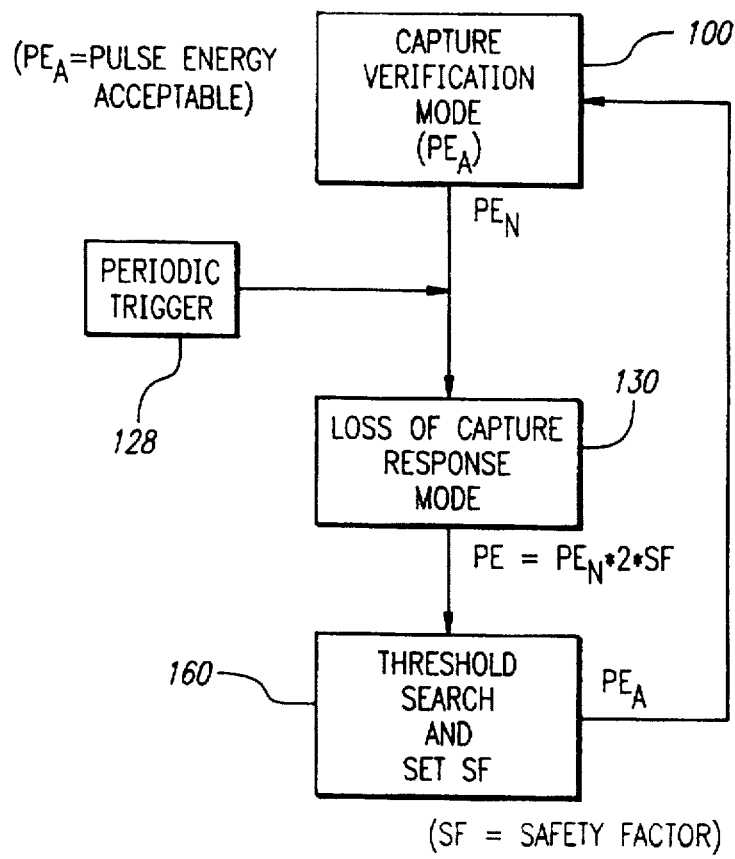
FIG. 5 shows an overview of the capture verification method of the present invention.

As seen in FIG. 5, the methods of the present invention are carried out by operating the pacemaker in different modes of operation, depending upon what is sensed, or not sensed, or the occurrence of other events. In a first mode, termed the Capture Verification Mode in FIG. 5, and shown at block 100 (note, in FIG. 5 and the other flowcharts presented herein, each main step or process is identified in a process "box" or "block", each of which has a reference numeral assigned thereto), the present stimulation pulse energy (PE) is checked to see if it is sufficient to effectuate capture. If it is, the pulse energy is acceptable, a condition referred to as "$PE_A$" (where $PE_A$ stands for "Pulse Energy Acceptable"). If the pulse energy is insufficient to effectuate capture, then the pulse energy is not acceptable, a condition referred to as "$PE_N$" (pulse energy not acceptable).

When the pulse energy is insufficient to effectuate capture, then the pacemaker switches to a Loss-of-Capture Response Mode 130. The Loss-of-Capture Response Mode 130 may also be invoked by a periodic trigger signal 128. The Loss-of-Capture Response mode sets the pulse energy to a high level, e.g., such that $PE = PE_N \times 2 \times SF$, where PE is the pulse energy, $PE_N$ is the prior pulse energy, and SF is a safety factor. Such a high pulse energy assures that capture will continue to occur until such time as the pulse energy can be readjusted to a more optimum value.

After a sufficient wait, to assure that the heart rhythm has stabilized using the high pulse energy set by the Loss-of-Capture Response Mode (block 130), a capture threshold search mode is undertaken (block 160). During the threshold search mode, the capture threshold is measured. Once the capture threshold is known, then the pulse energy is set to a value that will achieve capture, i.e., a new $PE_A$, as a function of the measured capture threshold and a safety factor. With the pulse energy set to $PE_A$ in this manner, the pacemaker then reverts back to the capture verification mode (block 100).

Figure 6:
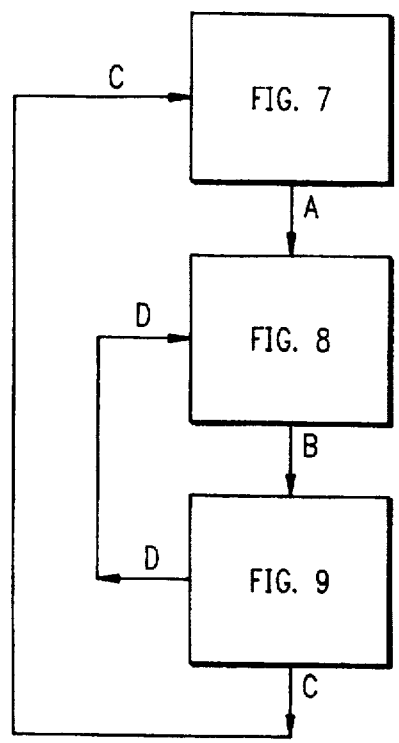
FIG. 6 is an overall flowchart of the capture verification method.

In FIG. 6, a more detailed flowchart is shown of the capture verification, loss of capture response, and threshold search modes shown in FIG. 5. FIG. 6 is a sufficiently large flowchart that it does not fit on one sheet. Hence, FIG. 6 is simply a map that shows how three flowcharts—FIGS. 7–9—are interconnected to provide the overall function described in FIG. 5 above.

Figure 7:
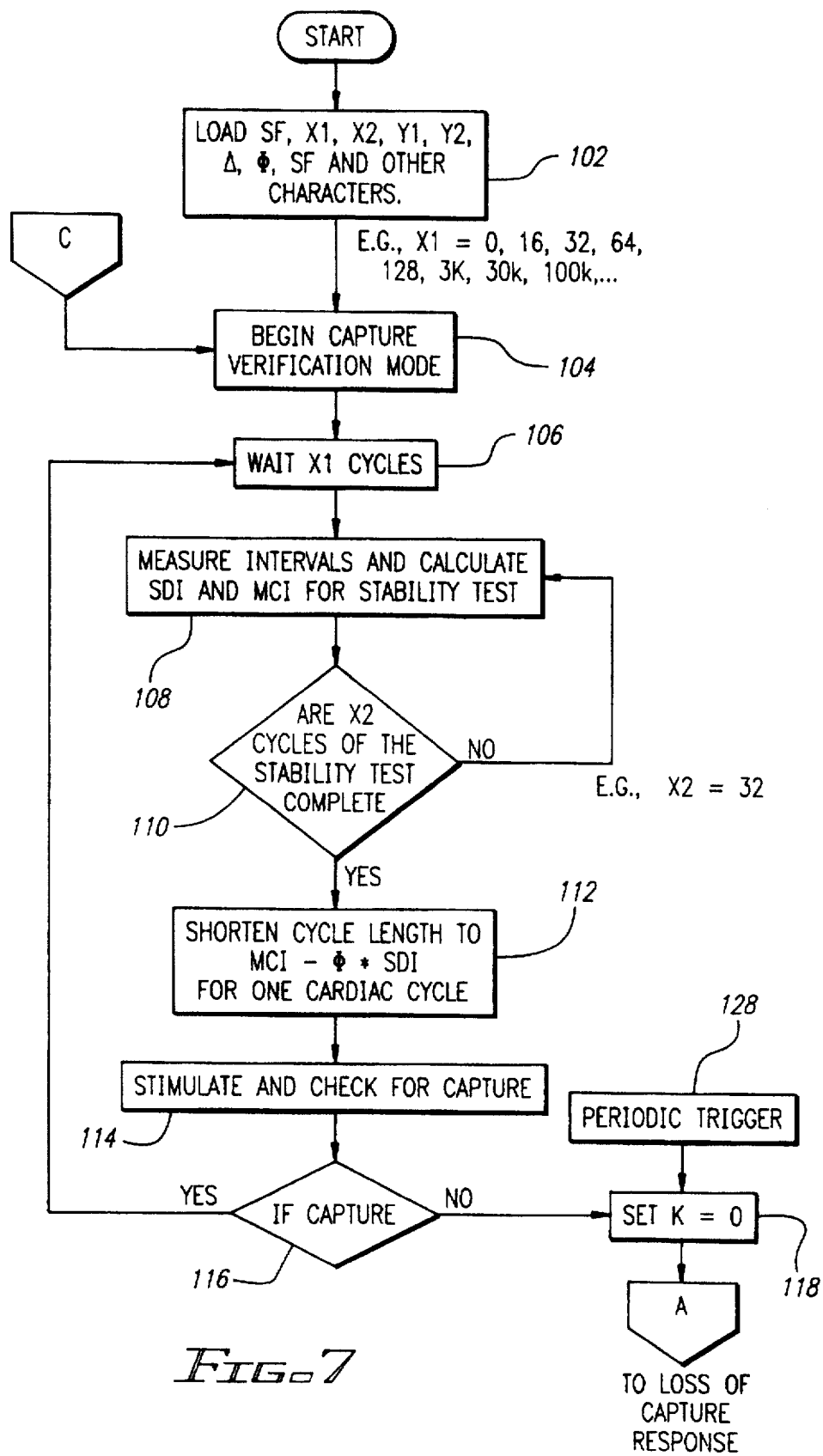
Figure 8:
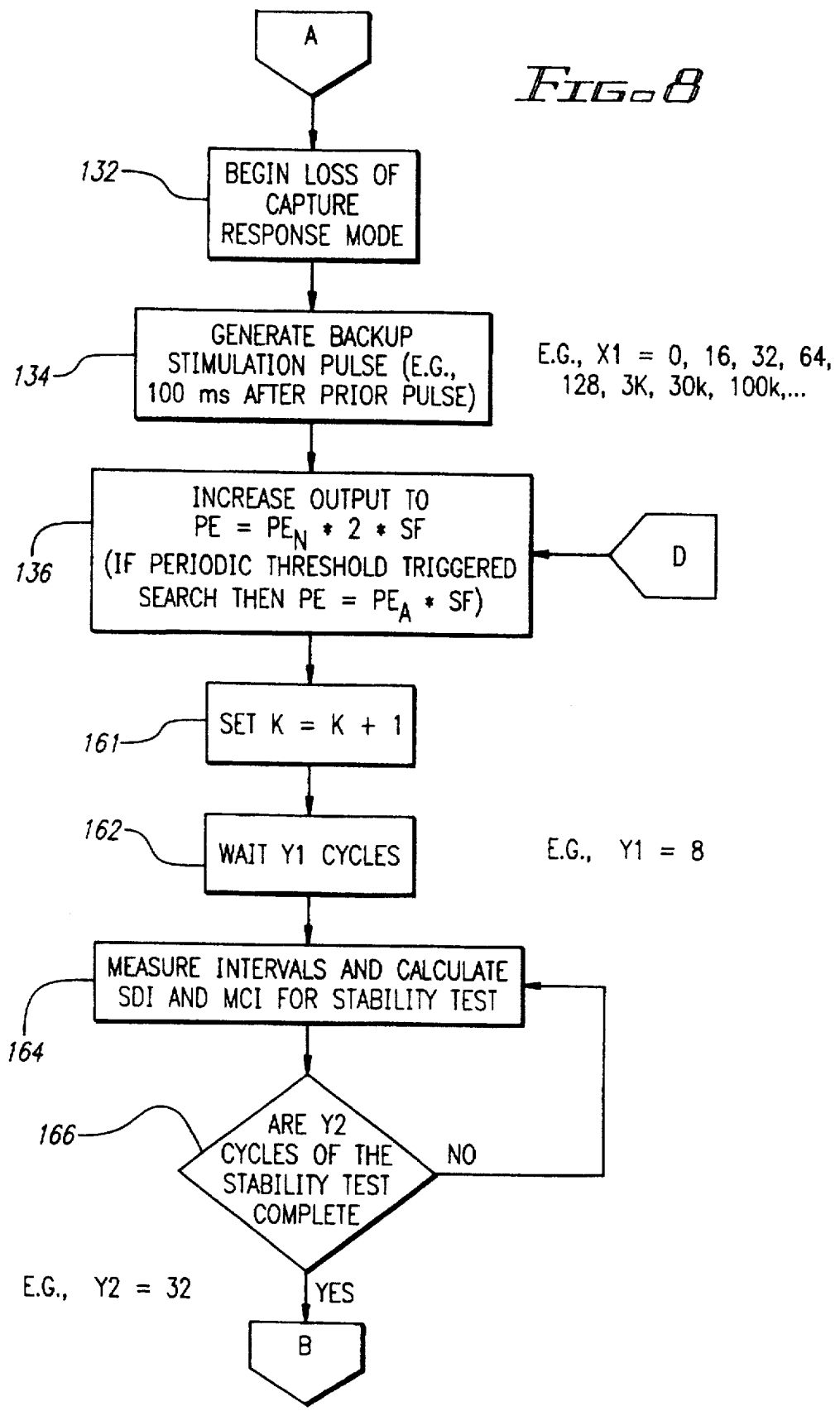

Starting initially with FIG. 7, but with reference in general to FIGS. 7–9, it is seen that the method first requires that certain control parameters be loaded into the memory of the pacemaker (block 102). Such control parameters include, in addition to the conventional pacemaker control parameters, a safety factor (SF), the length of certain waiting or test periods, X1, X2, Y1 and Y2, as explained below, and D, a step increment size. The length of the waiting and test periods may be expressed in either time units (e.g., seconds) or cardiac cycles.

After all the initial control parameters have been loaded into the pacemaker memory, the capture verification mode begins (block 104). A first step of such mode (block 106) is to wait for a period of X1 cardiac cycles (or X1 seconds, if the waiting period is defined in units of time). The waiting period X1 may be, e.g., 0, 128, 3K, 30K, 100K, . . . cardiac cycles, as selected by the cardiologist or attending physician. (A cardiac cycle is the time interval between successive ventricular events, e.g., the R-to-R interval.)

After waiting X1 cycles (or X1 seconds), a stability test is next performed for X2 cardiac cycles (block 108). Stability is determined by monitoring the time interval between selected cardiac events during a cardiac cycle, e.g., evoked potentials (i.e., the time interval between paced R-waves), or the time interval between intrinsic events, e.g., P-waves or R-waves. The stability may be estimated from the last X2 cardiac intervals. The cardiac intervals may be represented by the first cardiac interval, Interval$_1$, and the final interval may be represented by Interval$_{x2}$ while other intervals may be represented by the $i^{th}$ cardiac interval, Interval$_i$. Taking the sum of the last X2 cardiac intervals and dividing X2 cycles provides an estimate of the Mean Cardiac Interval, represented as MCI, for the last X2 cycles or:

$$MCI = \Sigma Interval_i / X2.$$

Next the Standard Deviation of Intervals between cardiac events for the last X2 may be used to estimate the variance of the cardiac cycles. This variable is represented as SDI and may be computed by using the following equation:

$$SDI = Square\ root\ of[\Sigma(Interval_i - MCI)^2/(X2-1)].$$

After X2 cardiac cycles are and the SDI and MCI have been estimated, then the pacemaker may leave the stability test blocks 108 and 110 and branch (yes branch in block 110) to perform a capture verification test.

Capture verification is performed using a relatively short cardiac cycle length in order to ensure that the pacemaker overdrives the native cardiac rhythm and thus avoids fusion. By assuming that the cardiac intervals are normally distributed over the last X2 cardiac cycles, an estimate can be made of the what cardiac interval the pacemaker should use in order to provide a very high probability of overdrive pacing for the capture verification test. The cardiac cycle length that may be used is for the capture verification test is:

*capture test cycle length=MCI−Φ·SDI,* where Φ has a value of about 1 to 5. The capture test cycle length is established by shortening the MCI by a number of standard deviations, Φ. Typically, Φ should have a value of 3 or 4.

Other stability tests may be used in addition to, or in combination with, the time-interval measurement method described. For example, stability may be determined by monitoring: mechanical events (e.g., contractions of the cardiac muscle tissue), lead impedance, systolic pressure, etc. Alternatively, the short cycle length that may be used for the capture verification test may be computed using a variety of methods other than the method described above. For example, the shortest of the X2 cycle lengths may be measured. The capture verification cycle length may then be set 30 milliseconds less than the shortest of the X2 cycle lengths. Another alternative is to simply to perform the capture test when the cardiac rhythm is deemed stable by some criteria. For instance, the capture verification test may only be performed if the SDI is less than 50 milliseconds. The pacemaker stays in a loop waiting for the SDI to achieve the required stability.

As shown in the flowchart of FIG. 7, once SDI and MCI have been estimated , then a capture verification test is performed by shortening the cardiac cycle length to the capture verification cycle length for one cycle (block 112) and then issuing a stimulation pulse (block 114). When performing capture testing in the atrium the shortened cycle is achieved, e.g., by shortening the VA interval or atrial escape interval of the pacemaker. When performing ventricular pacing in a single chamber pacemaker, the V to V interval is shortened for the capture verification test. When performing atrial pacing in a single chamber pacemaker, the A to A interval is shortened for the capture verification test. When the stimulation pulse issued after the shortened cycle is of sufficient energy to effectuate capture, an evoked response is immediately detectable following the delivery of the stimulation pulse. When the stimulation pulse issued after the shortened cycle is of insufficient energy to effectuate capture, no evoked response is detected. Thus, either an evoked response will immediately follow the stimulation pulse (when capture occurs) or it won't (when capture does not occur). Further, a sufficient short interval for the cardiac cycle length during the capture verification test virtually eliminates the possibility of fusion.

When capture occurs (YES branch of block 116), that means the current pacing energy is adequate ($PE_A$), and no further capture verification tests are performed until an additional X1 cycles have elapsed (block 106).

When capture does not occur (NO branch of block 116), that means the current pacing energy is inadequate ($PE_N$), and capture has been lost. When capture is lost, then a tracking flag K is set to zero (block 118) and the loss-of-capture response mode begins (block 132, FIG. 8).

The loss-of-capture response mode begins by generating a backup stimulation pulse a prescribed time delay after the prior pulse (block 134), which prior pulse was ineffective at achieving capture. For example, the backup stimulation pulse may be issued 100 msec after the prior ineffective stimulation pulse. After the backup stimulation pulse is generated, the pulse energy is then increased to a high level (block 136). Such high level assures that capture will be achieved (which is an important consideration for subsequent cardiac cycles) and also serves as a starting point for the subsequent capture threshold search. The pulse energy (PE) may be set, for example, to a value that is double the prior ineffective pulse energy ($PE_N$), times the safety factor (SF), or:

*$PE=PE_N \times 2 \times SF.$*

With the pulse energy at a high level, the threshold search mode begins by incrementing the tracking flag, K, (block 161). Then a waiting period begins (block 162) in order to allow the heart rhythm to settle down to a stable value. The waiting period may last, e.g., for Y1 cardiac cycles, where Y1 is a programmed control parameter. Y1 may be, for example, 8 cycles. (Alternatively, the waiting period Y1 could be measured in seconds, e.g., 5 seconds.)

After the Y1 waiting period, a determination is made, over a period of Y2 cardiac cycles, as to whether the cardiac rhythm is stable (blocks 164, 166). The same stability criteria may be used for this determination as described previously for the capture verification test (blocks 108, 110, FIG. 7). The value of Y2 is a programmed value set by the physician or cardiologist, and may be any suitable value from about 16 to 512, e.g., 32 cycles.

Once the cardiac rhythm stability has been estimated (YES branch of block 166), then the cardiac cycle is again shortened for just one cycle (block 168, FIG. 9), and a stimulation pulse is generated during the shortened cycle at a test pulse energy that is a prescribed increment lower than the prior pulse energy (block 172). In a preferred embodiment, the test pulse energy for the shortened cycle is set to:

*$PE_{test}=PE-K \times D$* where $PE_{test}$ is pulse energy of the current test pulse, PE is the stimulation pulse energy as calculated in block 136, D is a prescribed step increment of pulse energy (previously loaded into the pacemaker memory, as shown in block 102, FIG. 7), and K is the tracking flag.

Using the test pulse energy for the shortened cardiac cycle (blocks 168, 170), a determination is made as to whether the test pulse is of sufficient energy to effectuate capture (block 172). If capture does occur (YES branch of block 172), then that means the stimulation pulse energy is still above the capture threshold, and the process repeats by incrementing the capture flag (block 138), waiting for Y1 cycles (block 162), checking for stability criteria over Y2 cycles (blocks 164, 166), shortening the cycle length for just one cycle and stimulating the shortened cycle using a test stimulation pulse that is a step lower in energy than the previous pulse energy (blocks 168, 170).

If capture does not occur (NO branch of block 172), then that means that the pulse energy of the most recent test pulse is just below the capture threshold, or in other words, that the capture threshold was just crossed over between the prior test pulse (which did produce capture) and the most recent test pulse (which did not produce capture). Hence, the pulse energy is set to a value that is equal to the prior test pulse times the safety factor (block 174. Or, stated mathematically,

*$PE_A=[PE-(K-1)D] \times SF,$* where $PE_A$ is the newly determined pulse energy that is sufficient to produce capture.

After the new value of $PE_A$ is determined during the threshold search mode, the pacemaker then returns to the capture verification mode (block 104, FIG. 7), and the process repeats. That is, capture is verified on a sampled basis, e.g., after at least X1 cycles, and the loss of capture mode (block 132), and subsequent threshold search mode (block 161, et seq.), is invoked only if a loss of capture is detected during the capture verification mode. In this manner, the pacemaker thus maintains the stimulation energy at a value that is above the capture threshold, and periodically checks the capture threshold to reset the pulse energy, when needed.

The safety factor (SF) may assume any desired value. The safety factor may be, e.g., as high as 3 or 4, but typically it will be between about 1.7 and 2.2.

The periodic trigger (block 128) that starts the loss of capture response, followed by the threshold search mode that resets PEA, need only be invoked on an infrequent basis, e.g., 1–4 times per day. Otherwise, the loss of capture response and threshold search are only invoked when a loss of capture is detected.

Numerous variations in the above method may be made without departing from the overall approach of the invention, i.e., of verifying capture on a sampled basis, waiting sufficiently long for instabilities in the cardiac rhythm to settle down, and performing a threshold search on a periodic basis, or as invoked when loss of capture is detected. For example, the values of the waiting and testing periods, X1, X2, Y1 and Y2 need not be constants, but could themselves be variables depending upon the number of times that the capture verification test has been performed without loss of capture, or depending upon the value of the tracking flag K.

Further, when the pacemaker is a rate-responsive pacemaker, the control parameters that set the waiting periods, step increments, shortened pacing intervals, and safety factor, may also be automatically adjustable as a function of the physiological parameters that set the pacing rate.

As described above, it is thus seen that the present invention provides a method for verifying, on a sampled (but not over-sampled) basis, that an implantable pacemaker achieves capture with the stimulation pulses that it generates. It is further seen that whenever loss of capture is detected, a loss-of-capture response mode is automatically invoked, followed by a capture threshold search mode that searches for the capture threshold, and that when found, sets the stimulation energy of the pacemaker at a level that is a prescribed safety factor above such threshold.

Additionally, it is seen that the invention provides an implantable pacemaker wherein capture verification tests are performed by the pacemaker on a sampled basis only using a shortened capture test cycle length, thereby minimizing the likelihood of fusion interfering with the capture verification process, and wherein such capture verification tests are followed by capture threshold tests, when needed.

While the invention herein disclosed has been described by means of specific embodiments and applications thereof, numerous modifications and variations could be made thereto by those skilled in the art without departing from the scope of the invention set forth in the claims.

What is claimed is:

1. A capture verification method for use with an implantable stimulation device, comprising the steps of:

(a) operating the implantable stimulation device in a demand mode at a set stimulation pulse energy, the demand mode including sensing a patient's cardiac rhythm and inhibiting a stimulation pulse in the presence of an intrinsic cardiac signal;

(b) measuring the stability of the cardiac rhythm;

(c) determining, based on the stability measuring step, a shortened cycle length that is likely to exceed the cardiac rhythm;

(d) adjusting a current pacing cycle length to the shortened cycle length for at least one cardiac cycle; and (e) in the event the set stimulation pulse is delivered, determining capture threshold at the shortened cycle length.

2. The method of capture verification of claim 1, further comprising the step of:

(f) in the event the set stimulation pulse is inhibited, repeating steps (a)–(d) until a stimulation pulse is delivered.

3. The method of capture verification of claim 1, wherein step (e) comprises the steps of:

(g) verifying whether the set stimulation pulse energy achieves capture;

(h) in the event the set stimulation pulse energy does not achieve capture, measuring a capture threshold;

(i) resetting the stimulation pulse energy to a new value that is equal to the capture threshold plus a safety factor; and (j) repeating steps (a)–(f) with the new value of stimulation pulse energy.

4. The method of capture verification of claim 1, further including the step of:

periodically performing steps (e)–(g) in order to reset the stimulation pulse energy regardless of any prior capture verification.

5. The method of capture verification of claim 4, wherein the stimulation pulse energy is reset by performing steps (e)–(g) at least once every six hours.

6. The method of capture verification of claim 1, wherein the stability measuring step (b) comprises the steps of:

determining the stability over a programmable number of cardiac cycles.

7. The method of capture verification of claim 6, wherein the programmable number of cardiac cycles comprises at least 32 cardiac cycles.

8. The method of capture verification of claim 1, wherein the stability measuring step (b) comprises the step of:

determining the stability over a first prescribed period of time corresponding to a programmable number of seconds.

9. The method of capture verification of claim 1, wherein step (c) comprises the step of:

generating and delivering a first stimulation pulse at the currently set stimulation energy for one cardiac cycle at the shortened cycle length; and determining whether an evoked response immediately follows the delivery of the first stimulation pulse at the shortened cycle length, and if so, concluding that capture has occurred, and if not so, concluding that capture has not occurred.

10. The method of capture verification of claim 9, wherein:

step (c) further comprises generating a second stimulation pulse when the first stimulation pulse fails to effectuate capture, and delivering the second stimulation pulse a fixed time period after the delivery of the first stimulation pulse; and step (b) comprises verifying whether the cardiac rhythm is stable over a second period of time following the second stimulation pulse.

11. The method of capture verification of claim 1, wherein step (e) of measuring a capture threshold comprises the steps of:
   (1) increasing the set pulse energy to a high pulse energy which assures that capture will occur;
   (2) operating the pacemaker at the set pulse energy for a plurality of cardiac cycles so as to establish a cardiac rate;
   (3) generating and delivering a test stimulation pulse at the currently set pulse energy for one cardiac cycle at the shortened cycle length;
   (4) determining whether an evoked response immediately follows the delivery of the first stimulation pulse at the shortened cycle length, and if so, concluding that capture has occurred, and if not so, concluding that capture has not occurred;
   (5) in the event that capture has occurred, decreasing the pulse energy by a prescribed step amount and repeating steps (2)–(4); and
   (6) in the event that capture has not occurred, concluding that the pulse energy of the test stimulation pulse is roughly equal to the capture threshold.

12. A capture verification method comprising the steps of:
   (a) measuring the stability of a patient's intrinsic cardiac rate to ascertain if the intrinsic cardiac rate is within a prescribed limit;
   (b) providing an electrical stimulation pulse to the heart at a shortened pacing cycle length only when the measuring step (a) indicates that the intrinsic cardiac rate has remained within the prescribed limit; and
   (c) sensing whether an evoked potential occurs following the electrical stimulation pulse at the shortened pacing cycle length provided in step (b), and if so, verifying that capture did occur.

13. The capture verification method of claim 12, further comprising the step of:
   generating a backup stimulation pulse whenever capture is not verified in step (c).

14. The capture verification method of claim 12, wherein the specified number of cycles during which the intrinsic cardiac rate must remain within the prescribed limit comprises the number of cardiac cycles that normally occur within a 1∝2 minute time interval.

15. A method of setting the pulse energy of a stimulation pulse generated by an implantable pacemaker that minimizes the expenditure of battery current, comprising the steps of:
   activating a capture verification test only occasionally, on a sampled basis, after verifying that a stable cardiac rhythm exists; and
   invoking a loss of capture response mode if the capture verification test determines that capture is lost, the loss of capture response mode including:
      searching for an appropriate capture threshold; and
      when capture threshold is found, setting a stimulation energy of a stimulation pulse of the implantable pacemaker at a level that is a prescribed safety factor above the capture threshold.

16. The method of claim 15, further including the step of:
   invoking the loss of capture response mode on a periodic basis, whereby the capture threshold is measured and the stimulation energy is set at a value above the capture threshold whenever the capture verification test determines that capture is lost, or whenever periodically invoked, whichever occurs first.

17. The method of claim 15, wherein the step of activating the capture verification test comprises the step of:
   activating the capture verification test only after X1 cardiac cycles have elapsed, where X1 is at least 128 cardiac cycles.

18. The method of claim 15, wherein the verifying that a stable cardiac rhythm exists, comprises the step of:
   verifying that the cardiac rhythm is stable over at least 32 cardiac cycles.

19. An implantable stimulation device for maintaining a desired cardiac rhythm, comprising:
   timing means for defining a pacing interval, the pacing interval setting the lowest desired cardiac rhythm;
   pulse generating means for generating a stimulation pulse having a selectable pulse energy at the conclusion of the pacing interval;
   sensing means for sensing a cardiac depolarization corresponding to a contraction of cardiac muscle tissue;
   control means, coupled to the timing means, pulse generating means and sensing means, for inhibiting the pulse generating means and thereby preventing the stimulation pulse from being generated whenever the sensing means senses a natural cardiac depolarization before the end of the pacing interval, the control means further including:
      program means for operating the pacemaker at a set stimulation pulse energy for a first period of time so as to establish the desired cardiac rhythm, the first period of time including a multiplicity of cardiac cycles;
      verifying means for verifying, after the first period of time has elapsed, whether the cardiac rhythm is stable;
      capture verification means for verifying, once the cardiac rhythm is stable, whether the set stimulation pulse energy achieves capture;
      capture threshold measuring means for measuring the capture threshold in the event the capture verification means determines that the set stimulation pulse energy does not achieve capture; and
      pulse-energy setting means for automatically setting the pulse energy of the stimulation pulse at a level that is above the measured capture threshold by a prescribed safety factor;
   whereby capture is verified by the pacemaker only after the first period of time has elapsed, and thus only after a multiplicity of cardiac cycles have occurred, and then only when the cardiac rhythm is stable.

20. The implantable stimulation device of claim 19, further comprising:
   means for generating a periodic trigger signal for the capture threshold measuring means.

21. The implantable stimulation device of claim 19, wherein:
   the pulse generating means includes means for generating a backup stimulation pulse when the set stimulation pulse fails to effectuate capture, and delivering the backup stimulation pulse a fixed time period after the delivery of the set stimulation pulse; and
   the verifying means includes means for verifying whether the cardiac rhythm is stable over a second period of time following the backup stimulation pulse.

* * * * *